United States Patent [19]

Goettert et al.

[11] 4,258,644
[45] Mar. 31, 1981

[54] DEPOSITING LATENT FINGERPRINTS AND DEVELOPMENT THEREOF

[75] Inventors: Edward J. Goettert, Oakdale; George V. D. Tiers, St. Paul, both of Minn.

[73] Assignee: Minnesota Mining and Manufacturing Company, St. Paul, Minn.

[21] Appl. No.: 59,608

[22] Filed: Jul. 23, 1979

Related U.S. Application Data

[62] Division of Ser. No. 822,066, Aug. 5, 1977, Pat. No. 4,174,409.

[51] Int. Cl.³ .............................................. B05B 7/06
[52] U.S. Cl. .................................. 118/31.5; 118/264; 427/1
[58] Field of Search .............. 427/1, 7, 145; 428/485; 260/407; 118/264, 31.5

[56] References Cited

U.S. PATENT DOCUMENTS

| | | | |
|---|---|---|---|
| 2,334,850 | 11/1943 | Traylor | 260/407 |
| 2,341,239 | 2/1944 | Percy et al. | 260/407 |
| 3,239,545 | 3/1963 | Rogler | 260/407 |
| 3,251,869 | 5/1966 | Putnam | 260/407 |
| 3,377,286 | 4/1968 | Stricklin | 252/62.1 |
| 3,639,245 | 2/1972 | Nelson | 252/62.1 |
| 3,776,865 | 2/1973 | Glaser et al. | 260/407 |
| 3,823,022 | 7/1974 | Thomas | 427/145 |
| 4,069,235 | 1/1978 | Suzuki | 260/407 |

OTHER PUBLICATIONS

Research Disclosure–Jul. 1973.
Kirk–Othmer, *Encyclopedia of Chemical Technology*, 2nd ed., vol. 8, pp. 847–849, 1965.

*Primary Examiner*—Ronald H. Smith
*Assistant Examiner*—Janyce A. Bell
*Attorney, Agent, or Firm*—Cruzan Alexander; Donald M. Sell; William G. Ewert

[57] ABSTRACT

Latent fingerprints having a latency of several weeks are applied to paper substrates using compositions comprising trimeric aliphatic acids of at least 30 carbon atoms which are substantive to paper fibers are substantially non-volatile, and are non-hardening, non-toxic and non-hygroscopic. The latent fingerprints are developed as desired by dusting in the conventional manner with toner particles, suitably, comprising magnetic particles in oleophilic matrix.

4 Claims, No Drawings

DEPOSITING LATENT FINGERPRINTS AND DEVELOPMENT THEREOF

This is a division of application Ser. No. 822,066 filed Aug. 5, 1977 now U.S. Pat. No. 4,174,409.

This invention relates to a method for providing latent fingerprints having prolonged latency on documents as a means for identification and/or endorsement and to compositions therefor.

Because fingerprints are considered to be unique to an individual they provide a means of identification which is substantially infallible. Employment of fingerprints for identification or authentication purposes requires deposition of a fingerprint which can be compared either with known standards for purposes of verification or can be used as a means of identifying the individual who originally deposited the fingerprints if such identification becomes necessary. This constitutes a form of endorsement.

The method of fingerprinting widely used by law enforcement agencies in which the fingers are coated with ink and then applied to suitable forms is entirely unacceptable for identification on documents for various reasons. First the soiling of the hands antagonizes the individual whose fingerprints are being deposited. Further the fingerprints applied, for example, to a check can be smudged in handling or cause soiling of other documents.

The alternative procedure is to apply latent fingerprints to the document and subsequently develop them by some suitable procedure. Latent fingerprints from normal skin oils are well-known to be of only limited permanency, probably only a few days at most when applied to paper, and to have a tendency to smudging or disappearance as oils are transported in the fibers of the paper by capillarity throughout the paper. Because of these factors it is difficult to recover fingerprints from paper after more than a short period and the prints recovered are more likely to be those of the last persons to handle the paper and not those applied for identification purposes.

It is an object of this invention to provide invisible latent fingerprints on documents for purposes of identification and/or endorsement which possess prolonged latency and are susceptible to development substantially without interference from fingerprints arising from normal handling. Other objects will become evident herein elsewhere.

In accordance with the above and other objects of the invention it has been found that fingerprints formed after fingers are moistened by compositions comprising certain substantially non-volatile higher fatty polybasic acids surprisingly possess the desired permanency, are not dissipated or smudged by capillarity in a paper substrate and are readily developed by simple application of toner particles of various types even after periods as much as 1 to 8 or more weeks. Many other oily materials are found not to possess these unusual properties. The higher fatty polybasic acids are substantive to paper and to toner particles and are of the general formula $(C_nH_{2n-x}CO_2H)_y$ where n is from 10 to 20 and preferably 18 and x is a small odd integer and y is 2 to 4, preferably x and y are 3. Such preferred acids are often known as "trimer acids" because they are formed by trimerization of diunsaturated aliphatic acids. The structures may include branches and rings. Substantivity to paper is believed to be associated with the presence of three carboxyl groups. These higher fatty polybasic acids, in addition to being substantive to paper, are oleophilic and therefore are adherent to toner particles comprising an oleophilic matrix. The acids are further non-hardening and substantially non-volatilizable when exposed to air and are non-hygroscopic and non-irritating and provide invisible latent fingerprints.

The preferred polybasic acids have structures which are not readily shown by formula and are obtained as noted above by the polymerization of unsaturated fatty acids, e.g., linoleic acid. Trimeric acids are present in various proportions in many commercially available polymeric acids such as those sold under the Trademark name, Hystrene ® from Humko Products, Chemical Division, Memphis, Tenn. and Empol ® from Emery Industries Inc., Cincinnati, Ohio. Other sources of supply are available. The preferred trimeric polybasic acids tend to be oily or waxy materials of relatively high viscosity which can be described as honey-like. They may be used directly or by dilution in an oily base such as mineral oil, trioctyl phosphate, dialkyl phthalate or other neutral relatively non-volatile solvent. In general the composition should have an oily consistency without tackiness in order to be conveniently used. Properties of a number of such commercial products are tabulated in Table I.

TABLE I

| Commercial Name | % Acid Composition | | | Viscosity 25° C. (cSt) |
|---|---|---|---|---|
| | Monobasic | Dimer | Trimer | |
| Empol ® | | | | |
| 1010 | 0 | 97 | 3 | 5,200 |
| 1012 | 8–10 | 85–88 | 4–5 | 5,200 |
| 1014 | 1 | 95 | 4 | 5,600 |
| 1016 | trace | 87 | 13 | 5,300 |
| 1018 | trace | 83 | 17 | 7,500 |
| 1022 | 3 | 75 | 22 | 6,200 |
| 1024 | trace | 75 | 25 | 9,500 |
| 1028 | 6–8 | 72–77 | 17–20 | 6,100 |
| 1031 | 14–16 | 65–70 | 16–19 | 3,200 |
| 1040 | 0 | 20 | 80 | 60,000 |
| 1041 | 0 | 10 | 90 | 18,000 |
| 1054-A | 1 | 71 | 28 | ~11,000* |
| 1056-A | 2 | 79 | 19 | ~15,000* |
| Hystrene ® | | | | |
| 3695 | 1 | 95 | 4 | 6,800 |
| 3680 | trace | 83 | 17 | 8,000 |
| 3675 | trace | 75 | 25 | 9,000 |
| 5460 | trace | 40 | 60 | 30,000 |
| 3680 S | 1 | 84 | 15 | 14,000 |
| 3675 X | 1 | 87 | 12 | 9,300 |

*estimated

The composition selected is conveniently impregnated into an absorbent pad, such as an uninked stamp pad as could be used for rubber stamps, but, of course, free from colored ink. Other means of dispensing will be evident to those of skill in the art such as: individual strips of paper containing a small amount of the composition, sponges, felts, leathers, synthetic fabrics, etc. The finger or fingers (which terms herein include the thumb) which are desired to provide identification are moistened from the pad or paper strip and applied to a portion of the document or paper intended to carry the identification or endorsement. Greatest clarity will result by careful imprinting with slight rolling motion, but in the interest of convenience contacting, e.g., by merely grasping the document or paper will provide substantial identificatory markings. The imprinted document or paper, e.g. a check, is then handled in normal business procedures. When question arises as to the identity of the person who imprinted the document even 1 to 8 or more weeks later, the fingerprints are developed by dusting with toning powder such as those described in U.S. Pat. Nos. 3,377,286 and 3,639,245. A particularly convenient procedure is to make a brush of magnetic toning particles on a magnetized wand and draw the brush across the latent print. The latent print has sufficient affinity for the toner particles to remove them from the brush and unused particles are retained. This results in relatively little or no soiling from excess toner. Particularly preferred toner particles are colored black by powdered magnetite in a fusible base and the developed print can then be rendered permanent by warming to fuse the base and affix the particles to the fibers of the paper substrate. It will be evident that the present procedure and compositions provide a convenient tracing method for identification of passers of checks and in other situations, e.g. authentication of documents and the like. Such latent markings on the document are sometimes referred to as endorsements.

EXAMPLE 1

Pads of absorbent material, or artificial leather, are impregnated with each of several polybasic fatty acids and fingerprints are then imposed on various bond or security papers using light pressure. The papers are Hammermill Sentry Safety paper available from Hammermill Paper Co., Erie, Penn.; La Monte Safety Design paper available from La Monte Division of Georgia-Pacific Corporation, Warwick, N.Y.; Nekoosa white bond paper available from Nekoosa-Edwards Paper Co., Port Edwards, Wis.; and Timberline ® Safety Criss Cross from Boise Cascade Papers, Portland, Ore. Several prints are made of each material. Prints are developed at successive intervals using black magnetite-containing toner particles available commercially as "VHS" and "VQC ®" imaging powders (3M Company) and fixed by a suitable method, e.g. warming briefly. Comparison of the prints shows satisfactory legibility extending to periods of latency of up to 11 weeks. Such data are summarized in Table II.

TABLE II

| Fingerprinting Substance | Paper | Minimum Lifetime (weeks) |
| --- | --- | --- |
| Empol ®1054A | Hammermill Sentry Safety | 5 |
| " | La Monte Safety Design | 11 |
| " | Nekoosa White Bond | 11 |
| Empol ®1056A | Hammermill Sentry Safety | 1 |
| Empol ®1040 | La Monte Safety Design | 6 |
| " | Nekoosa White Bond | 6 |
| Empol ®1015 | Hammermill Sentry Safety | 1 |
| Empol ®1016 | La Monte Safety Design | 1 |
| Empol ®1010 | La Monte Safety Design | 1 |
| Hystrene ®3695 | La Monte Safety Design | 3 |
| Empol ®1054A | Timberline ®Safety Criss Cross | 3 |

EXAMPLE 2

Pads of filter paper are impregnated with Empol ® 1054A polybasic acids in concentrations of 100%, 90% diluted with 10% trioctyl phosphate and 75% diluted with 25% light mineral oil. In each case fingerprints are imposed on bond paper, or Safety paper and then developed by application of toner powder after 1 week. The prints are found to be clear and recognizable.

What is claimed is:

1. A fingerprinting pad consisting essentially of an absorbent pad at least partly saturated with a composition comprising polymeric acid of the general formula $(C_nH_{2n-x}CO_2H)_y$ where n is from 10 to 20, x is 1, 3 or 5 and y is 2 to 4 inclusive, wherein said composition moistens a finger upon contact of said finger with said pad.

2. The fingerprinting pad according to claim 1 wherein the trimeric acid is of the formula $(C_{17}H_{31}CO_2H)_3$.

3. A fingerprinting pad comprising an absorbent pad impregnated with a composition comprising a non-hardenable, substantially non-volatilizable, non-hygroscopic, non-toxic higher fatty polybasic acid substantive to paper, wherein said composition moistens a finger upon contact of said finger with said pad.

4. A fingerprinting pad according to claim 3 wherein said absorbent pad comprises paper.

* * * * *